United States Patent
Stenholm et al.

(10) Patent No.: US 6,627,443 B1
(45) Date of Patent: *Sep. 30, 2003

(54) COLORED COMPOSITION

(75) Inventors: Åke Stenholm, Upplands-Väsby (SE); Lars Karlsson, Norsborg (SE); Anders Löfgren, Hägersten (SE); Bo Nystrom, Sollentuna (SE); Otto Skolling, Solna (SE)

(73) Assignee: Fresenius Kabi AB (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/559,973

(22) Filed: Apr. 27, 2000

Related U.S. Application Data (62) Division of application No. 08/897,032, filed on Jul. 18, 1997, now Pat. No. 6,093,572.
(60) Provisional application No. 60/023,222, filed on Aug. 5, 1996.

(30) Foreign Application Priority Data

Jul. 19, 1996 (SE) .............................................. 9602818

(51) Int. Cl.$^7$ .............................................. G01N 33/00
(52) U.S. Cl. .............................. 436/1; 422/56; 422/57; 436/2; 436/3; 436/5; 436/127; 436/136; 436/138; 436/166
(58) Field of Search ........................ 422/56, 57; 436/1, 436/2, 3, 5, 127, 136, 138, 166

(56) References Cited

U.S. PATENT DOCUMENTS

| | | | | |
|---|---|---|---|---|
| 3,375,078 A | * | 3/1968 | Dendy | 422/79 |
| 5,362,633 A | * | 11/1994 | Pugia | 435/13 |
| 5,415,809 A | * | 5/1995 | Elson et al. | 116/206 |
| 6,007,529 A | * | 12/1999 | Gustafsson et al. | 604/410 |
| 6,093,572 A | | 7/2000 | Stenholm et al. | 436/1 |
| 6,398,771 B1 | * | 6/2002 | Gustafsson et al. | 604/410 |
| 6,399,387 B1 | * | 6/2002 | Stenholm et al. | 436/1 |

FOREIGN PATENT DOCUMENTS

| | | |
|---|---|---|
| EP | 0 228 819 | 11/1986 |
| SE | 9601348 | 4/1996 |
| WO | 93/24820 | 12/1993 |
| WO | 95/29394 | 11/1995 |

OTHER PUBLICATIONS

Eur.Ph. VI 2.2.3.
Dialog Abstract, Accession No. 004379627, WPI Accession No. 85–206505/34, TOA GOSEI Chem Ind Ltd: "Low temp. storing dried sheet potato in air–impermeable vessel together with deoxygenating agent; Polyvinyl Chloride"; & JP,A,,60130339, 850711, 8534 (Basic).

* cited by examiner

*Primary Examiner*—Jill Warden
*Assistant Examiner*—LaToya Cross
(74) *Attorney, Agent, or Firm*—Gilberto M. Villacorta; Serge Sira; Katten Michin Zavis Rosenman (57) ABSTRACT

The present invention relates to new color compositions which are especially suitable to be used in oxygen indicators. The compositions comprise iron(II), an agent containing pyrogallol entities and an organic acid.

15 Claims, 5 Drawing Sheets

COLORED COMPOSITION

This application is a divisional of U.S. patent application Ser. No. 08/897,032, filed Jul. 18, 1997, now U.S. Pat. No. 6,093,572 which claims priority from U.S. Provisional Patent Application No. 60/023,222, filed Aug. 5, 1996 and from Swedish Patent Application No. 9602818-8, filed Jul. 19, 1996, all of which are incorporated herein by referenced.

FIELD OF INVENTION

The present invention relates to color compositions comprising iron(II), an agent containing gallic acid entities and an organic acid which are especially suitable to be included in an oxygen indicator. The inventive indicators enable improvements related to the production of containers for storing oxygen sensitive pharmaceuticals and other sensitive products.

BACKGROUND OF THE INVENTION

In the pharmaceutical industry it is strongly desired to develop containers of polymeric materials to replace traditional glass containers in order to provide less resource consuming, cheaper and more convenient packaging systems. It is, however, a considerable technical problem to develop safe and cheap containers made of polymeric material which can replace glass as a barrier forming material against the environment and be compatible with a variety of fluids including lipophilic fat emulsions for parenteral nutrition. There have been many attempts to introduce polymeric materials for such lipophilic agents, but problems with degradation from penetrating oxygen and migration of components from the polymeric material into the stored fluids, especially after sterilization with steam at autoclaving conditions have prevented a wide-spread commercial use.

A highly sophisticated container for long-time storage of fluids aimed for parenteral administration is disclosed in the Swedish patent application SE 9601348-7 which hereby is incorporated as a reference. By a careful selection of polymeric materials, this type of container is capable of withstanding steam sterilization when finally filled and assembled and yet form a suitable barrier against environmental oxygen to protect oxygen degradation sensitive components during storage without involving any material that is incompatible with lipids. This container consists of an inner container, having one or several compartments for storage of drugs which readily can be mixed, just prior to the administration, enclosed in a substantially airtight outer envelope. In the space between the inner container and the envelope, an oxygen scavenging composition is placed to consume residual oxygen and the small amounts of oxygen penetrating through the envelope. To improve on the safety of the product, an oxygen indicator can be placed between the envelope and the inner container through which the transparent envelope visually indicates an oxygen leakage by a change in color. Especially for such oxygen sensitive products like parenteral nutrients comprising polyunsaturated fatty acids and certain amino acids, there is a demand to have simple and reliable indication of the integrity of the products, since many of the patients dependent on such a therapy are confined to self-administration in their homes with a supply of containers.

The demands of an oxygen indicator for a medical container for parenteral nutrients are equally high as the other features of the container. It must be capable to withstand autoclavation procedures (steam sterilization at about 121° C. for a prescribed time period, usually about 19 to 20 minutes) without losing its characteristics. It must consist of safe and non-toxic components which have a negligible tendency to migrate and waste the stored products and it must be fully compatible with the remaining parts of the container. The indicator function must be suitably sensitive and reliable so a distinct change in color visualizes a predetermined exposure to oxygen and thus the potential waste of the product which then must be discarded. In addition, a functional oxygen indicator should be cheap and easy to produce and assemble with the package.

Conventional visual oxygen indicators known to the art used in the form of tablets inside packages for pharmaceuticals or certain food products, such as Ageless-Eye KS from Mitsubishi based on methylene blue as a coloring agent, will not be able to withstand autoclavation. After autoclavation, the color change will be less distinct and instead of a homogenous blue color, a patchy or stained blue to pink colors will appear that severely impairs the sensitivity of their oxygen indicating capacity. This type of indicator is also normally recommended with a limited shelf-life of six months.

Oxygen indicators agents may also be possible to disperse in the polymeric packaging material, as suggested in the International patent application WO 95/29394 to W. R. Grace & Co. This material have a drawback in that its riboflavin indicator component is sensitive to heat and will not withstand autoclavation with maintained capacity. It would also be wasted by high temperature welding processes of the packaging material. Obviously, there still is a desire for improvements related to oxygen indicators. Especially to find reliable, cheap, non-migrating visual oxygen indicators to be included in container systems storing oxygen sensitive parenteral drugs intended to be steam sterilized after their final assembly.

The present invention aims to provide new color compositions suitable to be comprised in an oxygen indicator as well as being incorporated in water based surface treatment compositions.

It is an object of the present invention to provide improved oxygen indicators based on said colored compositions which are especially suitable to be a part of a container for long-time storage of oxygen sensitive pharmaceuticals for parenteral administration.

Another object of the present invention is to provide an oxygen indicator which can withstand autoclavation without losing any important characteristics and which has suitable characteristics for being assembled with a container for storing oxygen sensitive pharmaceuticals.

A further object of the present invention is to provide an oxygen indicator which is composed of constituents with less potential toxicity and thereby being especially suitable for the pharmaceutical and the food industry.

A still further object of the invention is to provide an oxygen indicator with high reliability which may serve as guarantee that patients dependent on parenteral nutrition not will infuse accidentally oxidized solutions.

DESCRIPTION OF INVENTION

The present invention relates to a color composition comprising an agent containing pyrogallol entities, and an iron (II) salt and an acid.

The salts of iron (II) useful in the present invention must be readily soluble to avoid the formation of precipitations of poorly soluble complexes with other components of the color composition. Preferably, the iron(II) salts are selected from a group consisting of iron(II)sulfates, iron(II)acetate, iron(II)nitrate, iron(II)chloride and iron(II)trifluoroacetate.

The agent containing pyrogallol entities are capable of complex binding iron(III), thus forming a colored product. It may consist of pyrogallol derivatives preferably gallic acid and its derivatives, particularly various esters of gallic acid. However, pure pyrogallol or gallic acid (which is carboxylated pyrogallol) can also be used, in particular when the toxicity of pyrogallol can be controlled or is of limited importance. A suitable agent is tannin of natural, synthetic or semi-synthetic origin comprising ester bridges in a network between a plurality of gallic acid entities.

The acid component is preferably selected to avoid the formation of poorly soluble complexes with iron ions and it should not be so strong that it hydrolyses the agent having gallic acid entities to free gallic acid which should be avoided since it may modify the predicted color characteristics of the composition. Preferably, an organic acid having at least two carboxylic groups is selected for the color composition and most preferably an organic acid having general formula $HOOC-(CR_1R_2)_n-COOH$, wherein $n=1-4$, $R_1$ is hydrogen or a hydroxyl radical, and $R_2$ is hydrogen or a carboxyl radical. In order to obtain a reversible color reaction, an alpha-hydroxy acid having at least two carboxylic groups, such as citric acid is suitable as the acid component in the color compositions.

From this information, it is possible to select alternative functioning iron(II) salts and acids of suitable strength for the color composition. However, the most preferred color composition according to the present invention comprises iron(II) sulphate or iron(II) sulphate heptahydrate as an iron(II) salt and citric acid or citric acid 1-hydrate, as an acid. Especially suitable color composition comprises (A) iron(II)sulphate or iron(II)sulphate heptahydrate, (B) a tannin as the pyrogallol entity containing agent and(C) citric acid or citric acid 1-hydrate optionally in combination with an appropriate carrier agent. The amounts of the components (A), (B) and (C) in the inventive composition preferably have the following relationships; (A):(B) is between 4:1 and 1:2 and (C):(B) is between 6:1 and 1:1. The carrier agent is suitably a cold swelling starch and preferably propyleneoxide ether of starch which gives the composition a certain viscosity and acts as a filling agent. Also other conventional thickeners, such as carboxymethyl cellulose (CMC), and diluents giving the composition a desired viscosity or adhesion, are conceivable to introduce in the compositions both as complements and substitutes to the starch.

When being exposed to environmental air, a preferred color composition will change color after a certain time. In the originally pale yellow composition, the iron(II)sulphate is oxidized in air to iron(III) which reacts with the aromatic system of the tannin, resulting in a change of color to black from the formed complexes between iron(III) and tannin. Originally, the composition will have a pale yellow color basically derived from the tannin. When exposed to oxygen, the iron will be oxidized to iron(III) which starts to react with the aromatic system of tannin molecules and a resulting green color and subsequently black color will appear. An important characteristic of the inventive color composition, is its color reaction reversibility. The system can be reversed in an oxygen free atmosphere back to its original pale yellow color by subsequent reduction of iron ions.

The mechanism behind the color reaction can be explained with that the gallic acid entities of the tannin is capable forming relatively stable pyrogallol anions which either may form a black complex with Fe(III), or react with oxygen to form a radical. The radical pyrogallol entity can also react with Fe(II) to form the black complex.

By varying the amounts of citric acid, the time to the color change can be controlled. In a colored composition comprising a water solution of 2% $FeSO_4$, 1.3% tannin and 3.5% citric acid, a color change is observed after about 4 hours. Increasing amounts of citric acid will substantially prolong the time to the color change by delaying the oxidation of Fe(II) to Fe(III). The system may also be controlled by varying the amount of tannin, since higher amounts of this constituent gives darker colors. An increase in the amounts of tannin and Fe (II), respectively, in an indicator composition will shorten the time to a color change to the final black color.

The inventive color composition has a sensitivity to environmental oxygen which makes it highly suitable for the use as an oxygen indicating composition, while its aesthetic appearance and conservative capacity gives it a high potential as a main ingredient in water-based surface treatment agents.

An especially preferred embodiment of the present invention refers to an oxygen indicator comprising the above mentioned compositions. The indicators are suitable to determine if the level of oxygen penetrating into a controlled oxygen depleted atmosphere is high enough to provide a color change of the indicator. Oxygen indicators according to the present invention consist of the mentioned color compositions optionally combined with a carrier.

The carrier is preferably an enclosing package formed membrane made of a polymeric material through which oxygen can permeate, but also impregnated strips of a porous material and hydrogels are conceivable alternatives as carriers. Alternatively, the oxygen indicator can be formulated as a tablet, in the form of pellets, formulated in a hydrogel or compounded into various solid or semi-solid carries generally known to persons skilled in this technique. For example, the oxygen indicating colored composition can be mixed with a suitable carrier composition which is conventionally used in tabletting or pelletization procedures. Another alternative is to include the indicator in a layer in a multilayered polymeric material prepared by lamination or coextrusion. The indicator composition may then be dispersed and evenly distributed in a melted polymer material which is formed into layer in multilayered polymeric film structure suitable for the manufacturing of containers with conventional technology.

Especially in applications related to the pharmaceutical industry, the oxygen indicators based on the colored composition, must be possible to steam sterilize in an autoclavation process and be compatible with the other components of a container filled with pharmaceuticals. For this reason, the carrier should also be capable of such a heat treatment and it is suitable to enclose the indicator composition in a small sachet or bag of a similar material as the container containing the degradable pharmaceuticals with which it is aimed to be stored. To enable a correct indicator function it is a prerequisite that the material enclosing the indicator admits oxygen transport. Preferred materials are based on polyolefins and may comprise thermoplastic elastomers to improve on their mechanical properties. Especially suitable are materials based on polyethylene and/or polypropylene and their copolymers. An especially preferred material typically will consist of a multilayered structure and contain a high amount of polypropylene. An example of such a material is Excel® from McGaw Inc. which is described in the European patent specification 0 228 819 and also in the mentioned Swedish patent application SE 9601348-7.

The described indicators according to the present invention have unexpected resistance against heat treatments and will maintain intact oxygen indicating capacity even if treated by sterilizing steam at 121° C. for more than 19 to 20 minutes and has been demonstrated to withstand such conditions for at least 60 minutes.

It has been noted that certain color compositions according to the present invention are light sensitive and may change color spontaneously if stored in intense light, including daylight, irrespectively of the oxygen exposure. This reaction is believed to originate from the ability of the organic acid (citric acid) to complex to Fe(III) ions and reduce said ions to Fe(II), in the presence of light. In this process, the citric acid entity will rearrange and split off carbon dioxide to eventually form acetone. However, if the indicator has reached the stage of an essentially black color, the black precipitates thus formed will not be possible to reverse and the color will remain black, irrespective of the light conditions. If, on the other hand, the indicator only has reached the green color state, this color can be reversed to the original pale yellow color if a sufficient amount of light is present. For these reasons, it may be suitable to enclose the inventive oxygen indicator color which are sensitive or suspected to be sensitive for light in a package which has been made light absorbing or light shielding to protect the composition from light of frequencies of a color affecting influence. The enclosing packages can thus be provided with a light protecting film or coating which has a capacity of removing the affecting light. Such films or other materials which can act as a filter for daylight or for UV-radiation are well known to persons skilled in the art and will not be discussed in more detail. Alternatively, for compositions having only a moderate or low light sensitivity, packages containing indicators based on the compositions, can be provided with instructions for storage in darkness.

An especially preferred colored composition for an indicator according to the present invention will comprise between 1 to 4 g of iron(II)sulphate or its heptahydrate, between 0.5 to 4 g of tannin, between 1 to 10 g of citric acid or citric acid 1-hydrate, and optionally between 2 and 15 g of a filling material, suitably propyleneoxide ether of starch and water up to 100 g. The filling material should be regarded as optional. The colored compositions are preferably enclosed in bags of Excel® having a size of about 0.5 to 2 ml. Specific examples of functioning indicator compositions are disclosed in the following detailed description of the invention. However, the skilled person will both be able to depart from these given frames and find especially suitable levels within them and yet fall within the scope of the present invention set out by the appended claims.

An oxygen indicator according to the present invention is prepared by mixing predetermined amounts of the iron(II) salt, the tannin and the acid to a homogenous composition. The resulting mixture is dissolved in water. This procedure preferably takes place in a controlled, substantially oxygen-free nitrogen gas atmosphere. The mixture is filled into bag shaped containers of Excel® or a comparable material which are sealed by means of welding in the controlled atmosphere. The indicators are stored in an oxygen-free atmosphere until they are assembled with the other parts of medical container. These indicators are especially suitable in transparent flexible containers of the type described in the mentioned Swedish patent application SE 9601348-7 (Pharmacia AB), consisting of an inner container with fluids for parenteral administration enclosed in an outer transparent air-tight envelope. When assembling this type of containers, an oxygen indicator and an oxygen scavenger are placed together with the fluid filled inner container in an enclosing envelope an oxygen-free or oxygen depleted controlled atmosphere, whereupon the envelope is finally sealed. The container can now be sterilized in its final condition before storage.

During a normal storage, the small amounts of oxygen remaining in the container and in the stored products and such oxygen diffusing through the envelope will be consumed by the oxygen scavenger and not be able to deteriorate the stored products or affect the indicator. However, if the container is erroneously assembled or accidentally damaged so environmental oxygen is leaking into it in a sufficiently large amount, the oxygen scavenger will be saturated and the surplus oxygen will react with the components of the indicator which will change color from pale yellow to green and after certain time to black. The skilled person will be able to make estimations about the time to change the color of the indicator and what level of oxygen is required for the change and predict how it will affect the oxygen liable stored products.

As discussed above, there is also a possibility to control the time to the color change by selecting different levels of the components of the indicator. It is also possible to adjust the reactivity of the indicator by selecting a higher surface to volume ratio of the enclosing package for the color composition compared to the container filled with the oxygen sensitive material. By a selection of such appropriate dimensional parameters, an obvious color change of the indicator can be obtained before the stored material is adversely affected by the oxygen. The manufacturer of container systems for the oxygen sensitive products thereby readily can provide them with suitable instructions for the user, by considering the indicator characteristics and the oxygen sensitivity of the products. For many practical applications, such as storing sensitive parenteral nutrients containing polyunsaturated fatty acids or amino acids, a prescribed color change of the indicator will be a clear indication for the user to discard the container.

Since the inventive indicators are not deteriorated in their capacity of visually indicating oxygen after conventional autoclavation procedures, they are especially advantageous to use in connection with storage packages of pharmaceutical products for parenteral use. Furthermore, they only contain components which have low or negligible tendency to migrate through polymeric materials frequently selected in medical containers like Excel® and other polypropylene containing multilayer films. The indicators contain only components which have a low toxicity and are cheap and simple to produce and they will consist of a color composition enclosed in small package of polymeric material which can be selected to be entirely compatible with materials of the medical container.

A further highly advantageous property of the inventive oxygen indicators is that they can be based on a color composition having a reversible color reaction. A storage in an oxygen-free environment can lead to that the reaction behind the color change is reversed if light is present, so a greenish indicator can be changed back to its initial pale yellow color after reduction of the iron(II) ions. A fully developed black indicator will however, not be reversed to its original yellow color. An important consequence of the reversibility of the color reaction is that the environment need not to be entirely or substantially oxygen-free when finally assembling the container comprising filled inner primary container, oxygen scavenger and oxygen indicator enclosed in the outer airtight envelope for storing oxygen sensitive products.

It is therefore possible to manufacture a container from an inner container made of a material which is at least partially penetrable for oxygen which is filled with the oxygen sensitive material and sealed under controlled circumstances, for example by means of inert gas. The inner container can be assembled in an atmosphere having normal, ambient oxygen level with an oxygen indicator according to the present invention and an oxygen absorber in an airtight, sealable, transparent envelope of a polymeric material, so as to form a final sealed container. The container will as a final step undergo sterilization by means of steam at 121° C. for at least 15 minutes (autoclavation) and preferably for about 19 to 20 minutes. Appropriate materials for the inner container, the outer envelope and the oxygen scavenger composition are disclosed in more detail in the Swedish patent application 9601348-7.

It is of a great advantage for simplifying the manufacturing process that the final assembly and sealing of the container for storage can be performed in an atmosphere of normal, ambient composition, however controlled from microbial contamination, without any laborious and expensive equipment for atmosphere control. For stored agents normally used in parenteral nutrition like lipid emulsions and amino acid solutions, the production of final container can be performed in an ambient atmosphere during a limited time period estimated to about 1 to 2 hours, when using indicators preferred according to the present invention and other materials as disclosed above. For other stored agents and other materials selected for the parts of the final container, it is possible to make estimations about the oxygen demand and arrive with safe instructions for the production of containers. The indicator reactivity can be modified, as disclosed above, to be adapted to various situations and levels oxygen exposure during its assembly with the container.

Besides being suitable as an indicator composition, the inventive color composition has good characteristics as a surface treatment composition, especially for articles of rough or untreated wood and iron. Since iron(II) in the presence of environmental oxygen will oxidize to iron(III), a composition with tannin and starch will form a difficult to dissolve black or blackish gray product. The presence of citric acid and iron sulphate will contribute to conserve the product from microbial degradation during storage. By the addition of another pigment, such as madder lake, a suitable for example an excellent red, surface treatment composition for outdoor use on wood can be obtained. In addition to its contribution to the color, the iron(II)sulphate will also serve as a powerful fungicide. A surface treatment composition according to the present invention will be advantageous over commercially available starch based composition for wood treatment, such as Falu Rödfärg, by its improved adhesiveness which will be especially apparent if up to 10 % (w/w) of linseed oil is added.

Color compositions according to the present invention will also be advantageous for surface treatment of iron products whenever it is desired to give them a blackish finish. The inventive color composition can simply be applied to the iron articles and dried whereupon an anti-corrosive black surface is obtained from the insoluble black complexes between iron and tannin. In order to obtain an excellently applicable iron surface treatment composition, up to 10 % (w/w) of linseed oil can be added to the color composition.

In Example 11 below, a composition suitable as a base for surface treatment composition is disclosed which shall be regarded as a non-limiting illustration to the capacity of inventive compositions of being used in applications for protective and decorative coating of various articles.

DETAILED DESCRIPTION OF THE INVENTION

EXAMPLE 1

A suitable color composition to be comprised in an oxygen indicator contains:

| Component | Amount (wt %) |
| --- | --- |
| Tannin (tannic acid) | 1.2% |
| Iron(II)sulphate heptahydrate | 1.8 |
| Citric acid 1-hydrate | 3.0 |
| Propyleneoxide ether of starch | 6.0 |
| Water | 88 |

Iron(II)sulphate heptahydrate can be substituted with iron (II)sulphate. Citric acid-1-hydrate can be substituted by citric acid. The amounts can be varied dependent on the desired magnitude and rate in the color change and the starch shall be regarded as an optional component.

Iron(II)sulphate heptahydrate was from Kebo (article no. 1.3965, Merck no. 1.03965). The tannin (puriss) and the citric acid 1-hydrate (puriss Ph Eur.) were from Kebo (article no. 15599, BDH no.30337 and article no. 1.5584, Merck No. 1.00242, respectively). A color composition according to above is prepared in a controlled atmosphere of nitrogen gas with less than 0.5 % oxygen. The composition is filled in bags made of Excel® having a dimension of 2×2 cm. Its original color is pale yellow. The bags are placed in environmental air in darkness, in order to study the change in color. After 3 to 4 hours, a distinct pale green color is apparent and after about 4 days, the color composition has turned into an almost black color.

EXAMPLE 2

Autoclavablity

Indicators made according to Example 1 are positioned in an outer airtight envelope, made of the material disclosed in the Swedish Patent Application 9601348-7, together with a water-filled inner container together with an oxygen absorber in a controlled atmosphere. This system is assembled to resemble a container aimed to stored parenteral nutrients and it is autoclaved at 121° C. for 19 minutes. The color composition is visually unaffected by the autoclavation and the rate in color change is unaffected in comparison with Example 1.

EXAMPLE 3
Reversibility

Indicators prepared according to Example 1 were subjected to autoclavation and thereafter exposed for environmental air for about 20 hours, whereupon a change in color from yellow to green was observed. The indicators exposed to air were subsequently stored in an oxygen-free environment. After 5 to 10 days storage under normal light conditions at about 100 to 500 lux, the indicators had regained their original pale yellow color.

EXAMPLE 4
Oxygen Detection Level

Indicators prepared in accordance with Example 1 were subjected to a controlled atmosphere of oxygen and nitrogen containing 0.2% oxygen. After 24 hours, a change in color to pale green was observed.

EXAMPLE 5
Long-time Storage Characteristics

Containers containing oxygen indicators were manufactured and autoclaved according to Example 1. These containers were placed in controlled environments at 25° C. and 40° C., respectively and was inspected after 1, 3, 6 and 12 months. The initial color of the indicator and the time interval to a change in color is observed. After twelve months storage, no visible changes in color was detected. As a reference, indicators not subjected to autoclavation has been stored under the same circumstances in an oxygen-free environment for twelve months without any detectable changes in color.

EXAMPLE 6

Experiments were performed in order to determine the change in color of the inventive oxygen indicators dependence on the amount of FeSO4, tannin and citric acid. These components were mixed in a controlled atmosphere with 14 g propylene oxide ether of starch in 200 g water. The mixtures were enclosed in small bags made of Excel® and stored in environmental atmosphere. The darkness (D) of the indicators was measured visually after 2, 24, 90 and 114 hours according to scale from 1–5, where 1 was graded as fair and 5 as very dark as demonstrated in Table 1 below.

From Table 1, it is obvious that if the concentration of citric acid is increased in the composition, a slower color change is observed. It is also obvious that an increase in the tannin leads to a more rapid color change of the indicator composition.

EXAMPLE 7

A preparation of an indicator composition for the determination of the rate in color change and further tests was prepared with the following composition:

| Components | Composition (g/L) |
|---|---|
| tannic acid | 13 |
| iron(II)sulphate heptahydrate | 20 |
| citric acid monohydrate | 35 |
| water | up to 1 liter |

Water for injection (WFI) of 85° C. was filled in a 15 liter vessel. The water was stirred and nitrogen bubbled through a lance during approximately 2 hours. The citric acid-1-hydrate was weighed and added to the water. Stirring and nitrogen bubbling continued during 10 minutes. The tannic acid and the iron(II)sulphate-7-hydrate was then added in the same way. The indicator solution was filled, through a 0,22 μm Millipore filter, on glass flasks of 5 L.

Filling of the indicator solution is performed in sachets made of Excel® film ( 38 mm). The film was converted from reels of 300–450 widths to a width of 38 mm. The reel of Excel film was placed on the carrier of an Inpac filling equipment. The Excel film was printed using a white hot-stamp foil. The film was double-folded and welded along the side and transversally. The glass flask with indicator solution was placed in a nitrogen-protected vessel above the filling station. The nitrogen overpressure was controlled during the filling process. Indicator solution flowed through a tube into the welded film and the transversal welding station welded a strip of indicators separated by welds of 6 mm. The volume of one indicator is approximately 1 ml.

Strips of 50 indicators were packaged in airtight overwrap bags of the material disclosed in the Swedish Patent Application 9601348-7 together with Z-100 oxygen absorbers.

EXAMPLE 8
Study of Indicator Color Transition

Oxygen indicators prepared in sachets according to Example 7 were taken out of the overwraps and placed in air. The time to the first obvious change in color, the time to an intense green color and the time to an almost black color were measured. Reference samples were kept inside overwraps to retain original colors for comparison.

The indicator color transition was also studied by measuring the absorbance of the indicator solution in absence of oxygen and as a function of time in air. The sachets were kept in the airtight overwrap bags with oxygen absorbers in daylight until the green color totally disappeared and the indicator was pale yellow. Indicator samples were taken out of the overwrap bags and filled in a spectrophotometer cell after 1, 3, 5, 24 and 48 hours of oxygen exposure. The absorbance was measured between 400 and 750 nm on a Shimadzu UV-265 spectrophotometer apparatus. A peak in the spectra at approximately 635 nm was used to describe the color change of the indicator solution.

The color of the indicator solution is transparently pale yellow in absence of oxygen. When exposed to air for 5 hours, using the standard composition described in Example 7, a change to green is obvious. This is followed by a continuous transition to darker green. After another 5 days in air the color of the indicator is almost totally black.

Figure 1:
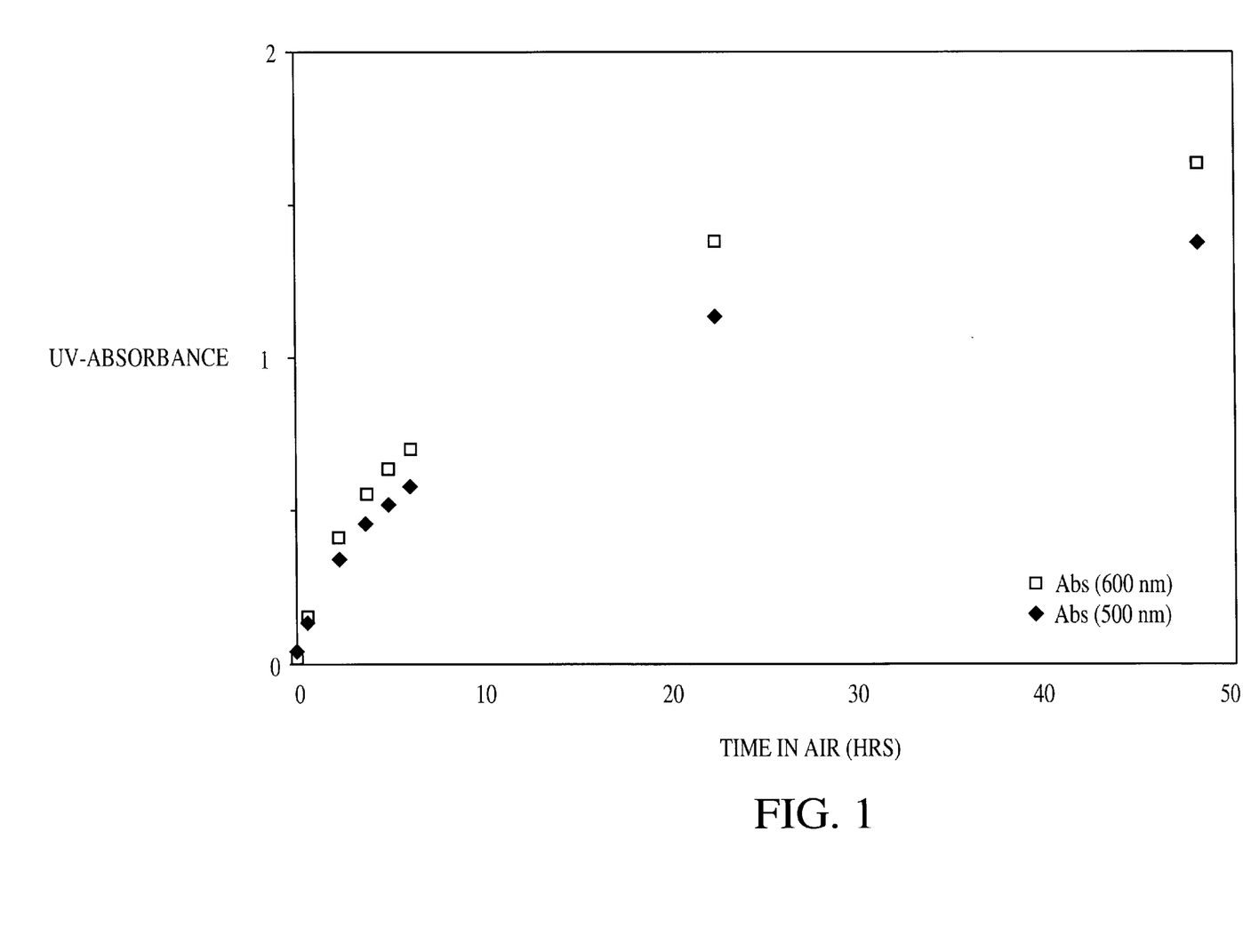
FIG. 1 shows the absorbance of the inventive indicators at 500 and 600 nm.

In order to describe the color change of the indicator solution UV/Visual spectroscopy was used. The results are presented in FIG. 1. Measurements at 500 nm and 600 nm give similar absorbance curves. A peak at 635 nm have been used to further describe the transition of the indicators in FIGS. 2, 3 and 4.

EXAMPLE 9

Study of Indicator Color Change at Different Temperatures and Light Intensities

The color transition of indicators of Example 2, from pale yellow to green as a function of temperature was studied. The oxygen indicators were kept at 5, 25, 40 and 50° C. in dark. A Shimadzu UV-240 spectrophotometer was used to measure the absorbances ( 635 nm) after 0, 1, 3, 5, 24 and 48 hrs in air.

The reverse color change of the indicators from green to pale yellow was studied at different intensities of light. The change in absorbance at 635 nm was measured after exposure to 0, 1800, 3900 and 8500 lux during 0 hrs, 1 hr, 3 hrs, 5 hrs, 24 hrs, 48 hrs, 7 days, 14 days and 21 days in air at 25° C. A Philips TLD/95 fluorescent tube was utilized as source of light. The light intensities in the study were measured with a Hioki 3423 luxmeter calibrated at 10, 100 and 1000 lux.

Figure 2:
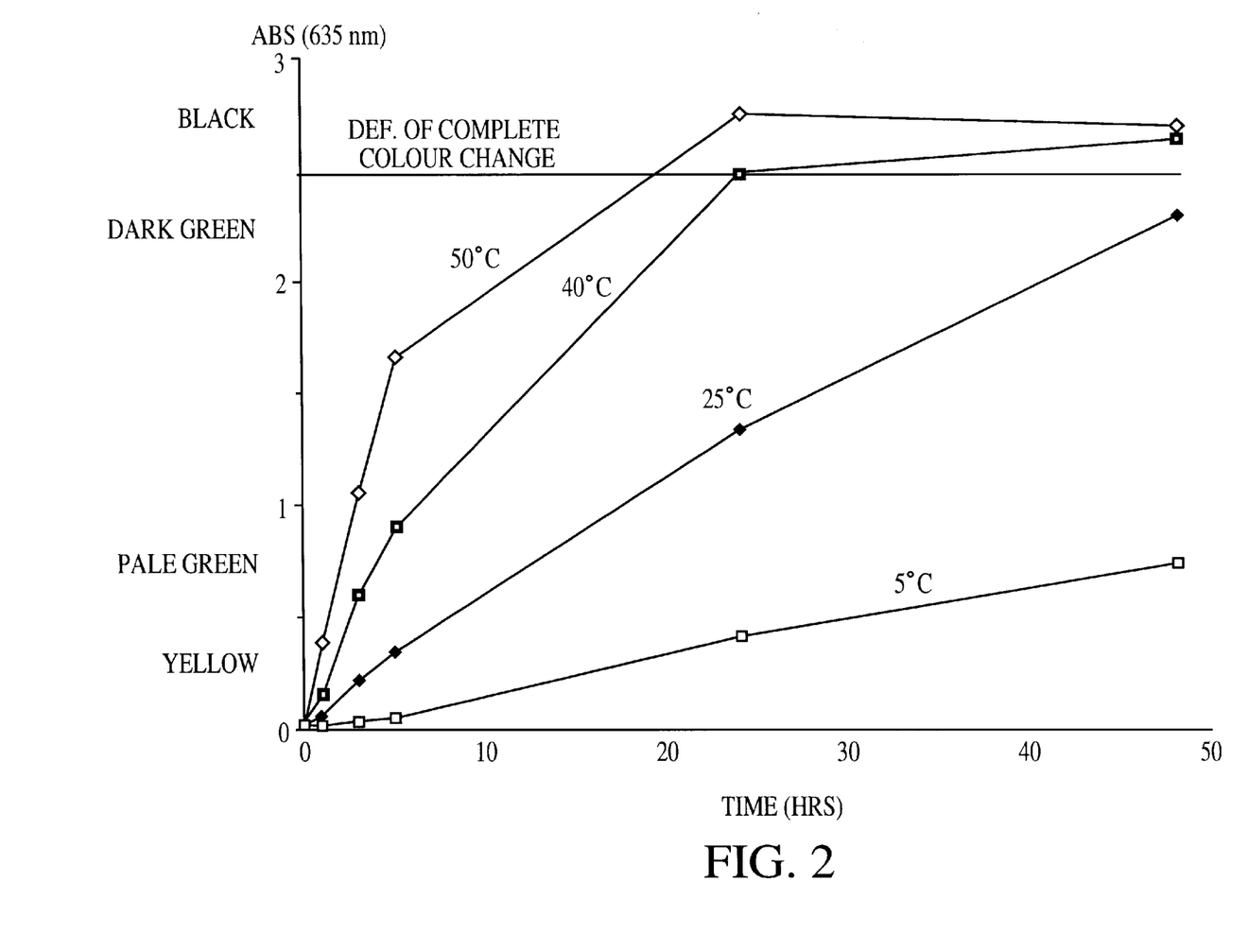
FIG. 2 demonstrates the kinetics of an indicator reaction at different temperatures in the absence of light. The definition of a complete color change to a dark green, opaque indicator is marked in the figure.

The influence of temperature on the kinetics of the color transition is shown in FIG. 2.

The absorbance of the indicator solution at 635 nm have been used to describe the color change at 5, 25, 40 and 50° C. when exposed to air under dark conditions. The oxygen-driven reaction strongly depends on temperature according to FIG. 2.

If a complete color change is defined by the absorbance value at 635 nm that corresponds to an indicator visually estimated as opaquely dark green (absorbance of approx. 2,5), the time to a color change at 5° C. is approximately 8 days, extrapolating the curve in FIG. 2. The complete change at 25° C. is obtained after 2–3 days.

The color transition of the indicator is controlled by two different mechanisms. An oxygen-driven reaction turns the indicator from pale yellow to green to black when exposed to oxygen and a reaction driven by light turns the indicator from green to pale yellow.

Figure 3:
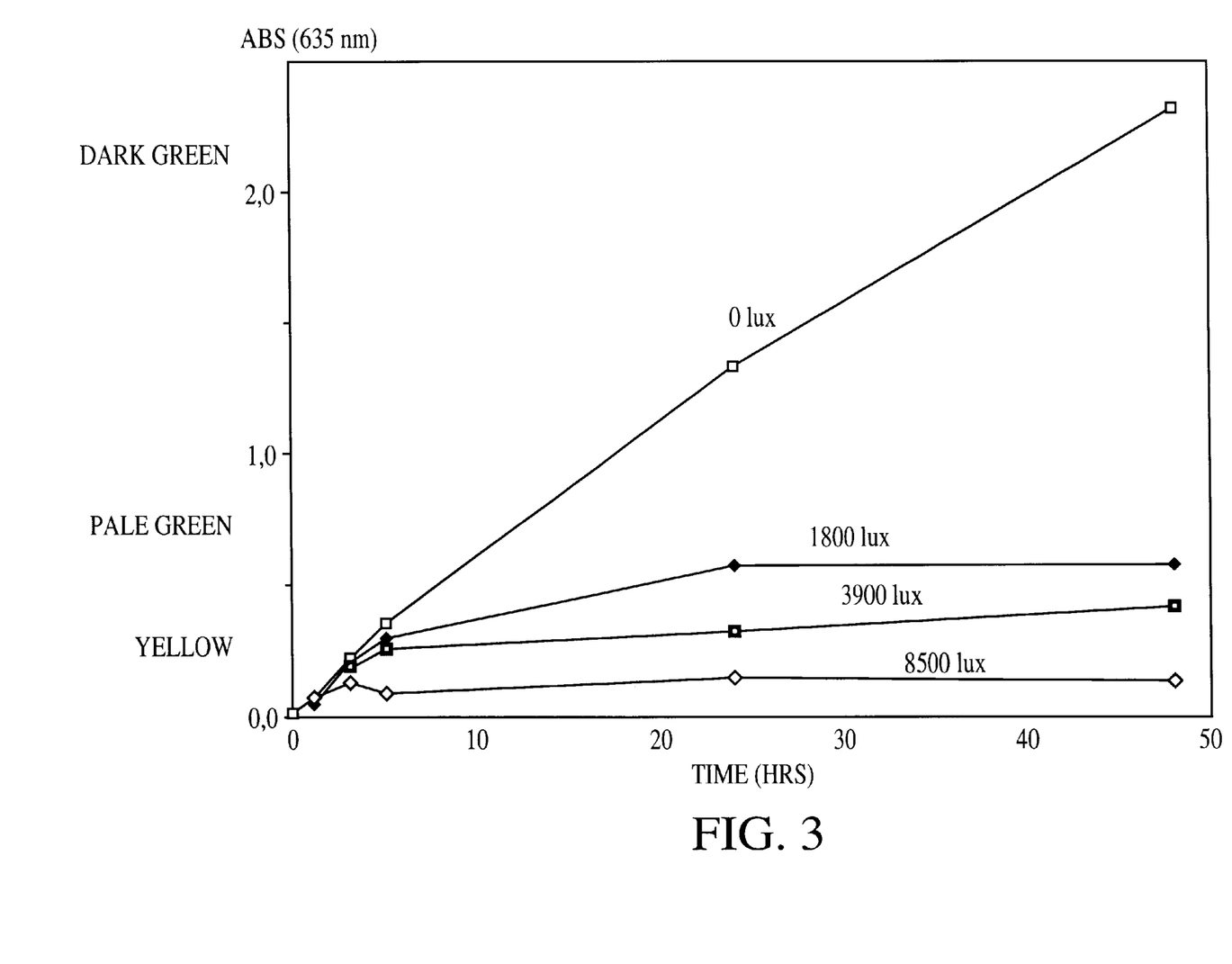
FIG. 3 shows the influence of illumination on the color change of an indicator according to the present invention. The estimation color of the indicator at certain absorbances is marked.

When the inventive oxygen indicators are exposed to light the kinetics of the color transition decreases as a function of the intensity of the light according to FIG. 3. When the intensity is high enough the reverse transition occurs and the indicator turns from green to pale yellow. Black indicators have not, however, been able to transform to the yellow state irrespective of the light intensity.

When exposed to air, the intensity of light must be substantial in order to prevent the color change from yellow to green (FIG. 3). When the indicator is placed in dark ( 0 lux) exposed to air, the color change described by the absorbance is more or less linear during the first 50 hours of exposure.

Figure 4:
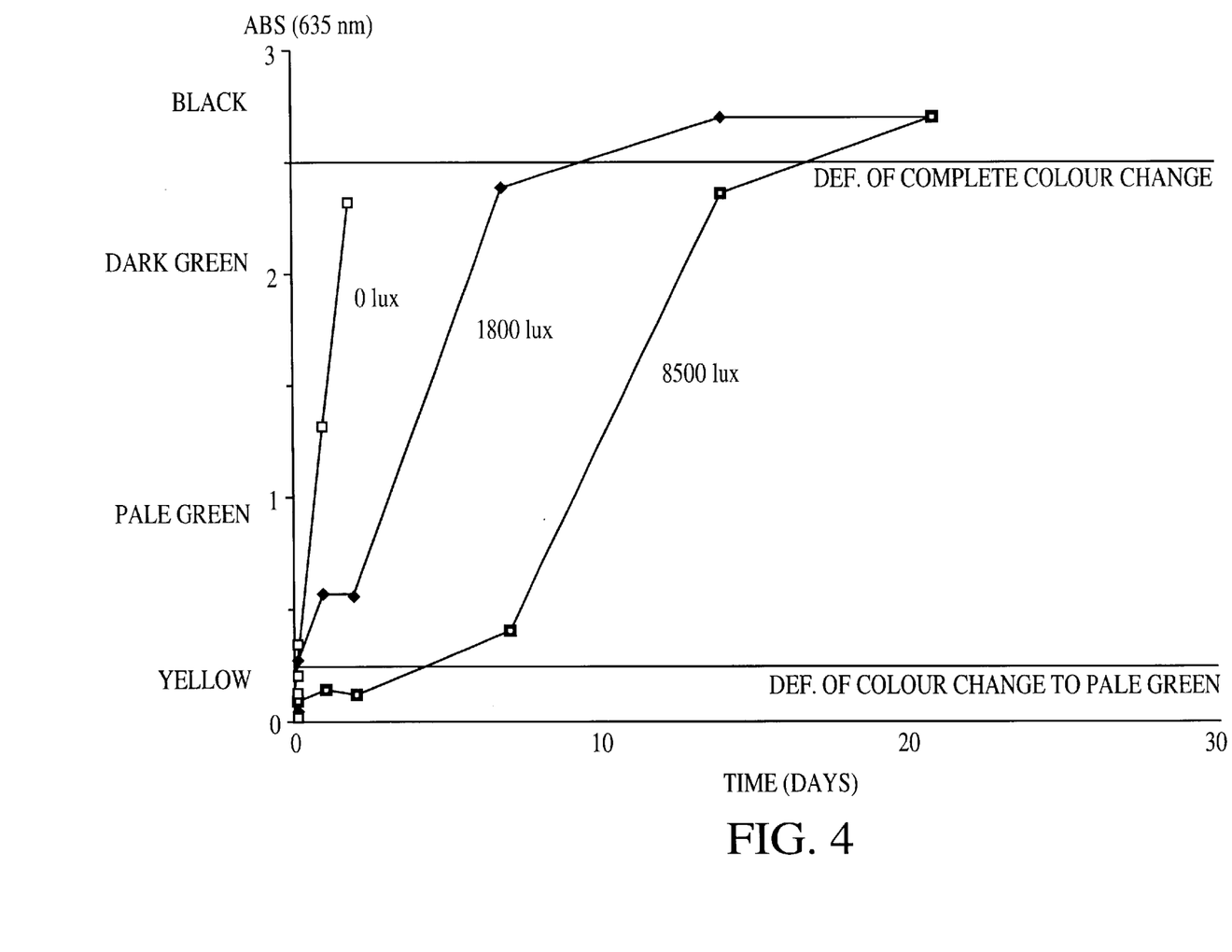
FIG. 4 demonstrates the influence of light on the color change of an indicator according to the present invention. The definition of a complete color change to a dark green, opaque indicator is marked in the figure.
Figure 5:
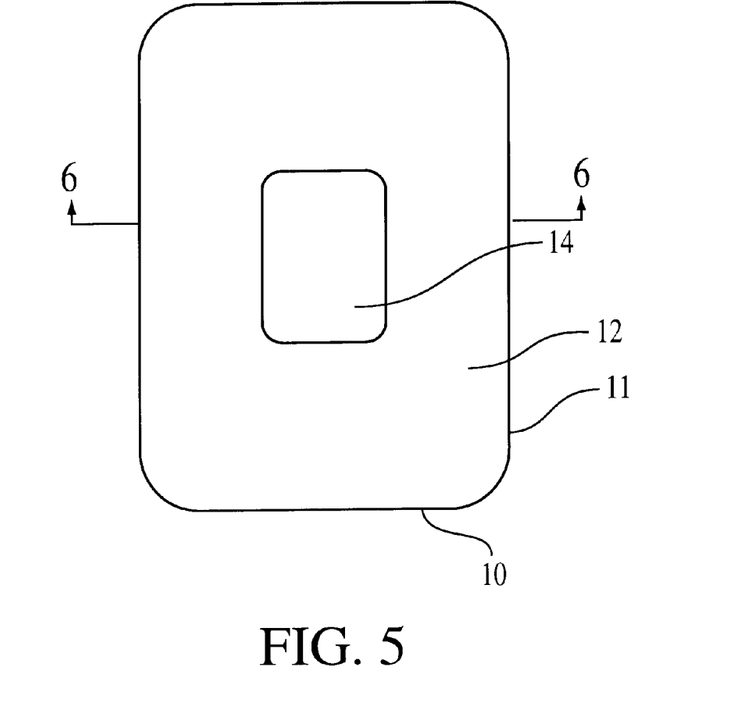
FIG. 5 is a top view showing the indicator sachet within a container.
Figure 6:
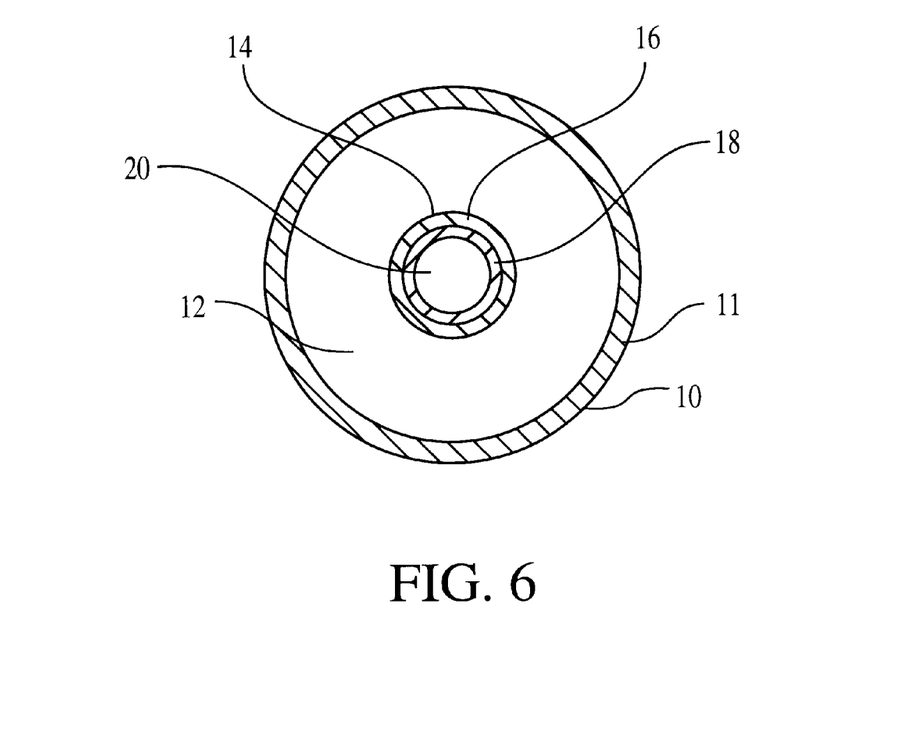
FIG. 6 is a cross-section view of an indicator sachet within a container.

When indicators are exposed to light the absorbance increases until it reaches a constant value that is dependent on the intensity of light. The color of the indicator at certain absorbances is marked in FIG. 3. The equilibrium lasts for approximately 3–4 days. The kinetics of the color change then increases again and the indicator is totally black after another 10 to 20 days depending on the light intensity (FIG. 4).

Normal room illumination at a distance of 1–2 meters from a fluorescent tube corresponds to approximately 500 lux. At a distance of 10 centimeters from a tube the light intensity is approx. 10000 lux and in direct sunshine values of 80000 to 90000 lux have been observed.

EXAMPLE 10

Migration Analysis

In order to study the migration of components in indicators prepared according to Example 7 to the infusion products, non-specific migration analysis according to the Eur. Ph. and specific migration analysis of tannic acid and possible degradation products from tannic acid were performed.

Analysis of non-specific migration from the indicators is performed according to the Eur. Ph., VI 2.2.3; "Plastic containers for aqueous solutions for intravenous infusion", performing Acidity or alkalinity, Absorbance and Oxidizable substances only. The oxygen indicators were placed in three different positions within the package. The normal position was close to the port. The "increased case" corresponded to three indicators placed in direct contact with the primary bag, jammed between the overwrap and the primary bag. A worst case study was performed by placing two indicators in the MilliQ-water inside the 100 ml Excel® primary bag. Steam sterilization of the worst case sample was performed during 60 minutes. Normal sterilization time is 19 minutes. Two reference samples were made without any indicators present.

The specific migration analysis of tannic acid and degradation products from tannic acid was performed with samples placed according to the unspecified migration analysis. The sachet samples were prepared by dissolving tannic acid and citric acid in MilliQ-water to a concentration of 1,2% (w/w) and 3,0% (w/w), respectively. The solution was filled in 1 ml sachets made of Excel® material. The 1 ml samples were placed together with MilliQ-water filled 100 ml Excel® bags in overwrap bags according to the Swedish Patent Application 9601348-7. The samples with the sachet placed in a normal position (close to the port) were steam sterilized for 19 minutes (normal cycle) and 60 minutes. The increased and worst case samples were sterilized for 60 minutes. A reference sample with no 1 ml sachet was sterilized for 60 minutes. The MilliQ-water was analyzed by HPLC in order to investigate if migration of tannic acid had occurred to the water. Gallic acid was used as a marker of degraded tannin.

The oxygen indicator has been analyzed regarding migration, both specific migration of tannic acid and unspecified migration according to Eur. Ph. VI 2.2.3; "Plastic containers for aqueous solutions for intravenous infusion", performing tests of "Acidity or alkalinity", "Absorbance" and "Oxidizable substances".

The unspecified migration analysis was performed with indicators in three positions within overwrap bags according to Table 2, below. The normal position is strictly according to the Eur. Ph. with the indicator close to the ports for additions and emptying. The increased position is defined as being between the inner Excel® bag and the outer bag. The worst case position means two indicators placed inside the primary bag and a sterilization time of 1 hour. Normal, increased and reference samples were sterilized for 19 minutes. The results in Table 2 are within the limits stated in the Eur. Ph. The UV-absorbance limit is 0,20 and the maximum allowed deviation from a blank sample regarding Oxidizable substances is 1,5 ml (volume of titration). No indications of migration of components in the oxygen indicator occur according to these analyses.

Calculations of the solubility parameters for pyrogallol and gallic acid were performed in order to predict the migration ability of these compounds through the Excel film. For gallic acid and pyrogallol the parameters are 30 and 35 $J^{1/2}$ $cm^{-3/2}$ respectively. The solubility parameter for the Excel material is approximated to 16 $J^{1/2}$ $cm^{-3/2}$ [6]. The big difference in parameter values indicates that the migration risk is negligible.

In order to verify the theoretical calculations above a migration study was performed. Gallic acid, a potential degradation product of tannic acid, was used as a marker of tannic acid. A worst case study was performed with an Oxalert placed inside the MilliQ-water inside the Excel primary bag and autoclavation occurred for 60 minutes. The normal autoclavation time is 19 minutes. The MilliQ-water samples were analyzed by HPLC. No gallic acid could be detected in any of the samples. The limit of the quantification was set to 1 µg/ml.

EXAMPLE 11

A suitable color composition serving as a ground formula for surface treatment applications:

| Component | Amount (wt %) |
|---|---|
| Tannin (tannic acid) | 1.3% |
| Iron(II)sulphate heptahydrate | 2.0 |
| Citric acid 1-hydrate | 0.7 |
| Propyleneoxide ether of starch from potatoes | 8.4 |
| Water | 87.6 |

TABLE 1

| FeSO4 (g) | Tannin (g) | Citric acid (g) | D 2h | D 24h | D 90h | D 114h |
|---|---|---|---|---|---|---|
| 6 | 1.6 | 4 | 1.5 | 3 | 4.5 | 4.5 |
| 2 | 1.6 | 10 | 1 | 2 | 3.5 | 3.5 |
| 6 | 3.6 | 10 | 1 | 3 | 4.5 | 4.5 |
| 4 | 2.6 | 7 | 1 | 2.5 | 4.5 | 4.5 |
| 2 | 3.6 | 10 | 1 | 2.5 | 4 | 4 |
| 2 | 3.6 | 4 | 1 | 3.5 | 5 | 5 |
| 2 | 1.6 | 4 | 1 | 2.5 | 3.5 | 3.5 |
| 6 | 1.6 | 10 | 1 | 2.5 | 3.5 | 3.5 |
| 6 | 3.6 | 4 | 1.5 | 4 | 5 | 5 |

TABLE 2

Unspecified migration according to Eur. Ph. VI 2.2.3

| indicator position | | Max. Absorbance (230–360 nm) | Acidity/ alkalinity | Oxidizable substances dev. fr. blank (ml) |
|---|---|---|---|---|
| indicator (normal pos.) | 1 | 0.027 | Passed | 0.5 |
| | 2 | 0.03 | Passed | 0.3 |
| indicator (increased pos.) | 1 | 0.018 | Passed | 0.3 |
| | 2 | 0.022 | Passed | 0.6 |
| indicator (worst case pos.) | | 0.037 | Passed | 0.6 |
| Reference sample (without indicator) | 1 | 0.031 | Passed | 0.6 |
| | 2 | 0.028 | Passed | 0 |

What is claimed is:

1. A method of preparing a transparent flexible container for storing a perishable fluid, which container visually indicates if the perishable fluid has been inadvertently exposed to environmental oxygen which method comprises the subsequent steps of:
    a) assembling together in a controlled atmosphere a transparent, airtight, outer sealing envelope and a primary container made of a partially oxygen permeable material such that a space is defined between the inner container and the outer sealing envelope, said inner container being filled with a perishable fluid;
    b) disposing an oxygen scavenging composition and an oxygen indicator having a reversible color reaction in said space, wherein the oxygen indicator comprises an aqueous solution of an agent containing a pyrogallol entity, a salt of iron (II), and an acid;
    c) sealing the airtight outer envelope; and
    d) subjecting the container to sterilization.

2. A method according to claim 1 wherein the container is assembled in an atmosphere of an ambient oxygen level.

3. A method according to claim 1 wherein the sterilization is performed by means of steam at 121° C. for at least 15 minutes (autoclavation).

4. A method according to claim 1 wherein the outer envelope and the inner container are multilayered.

5. A method according to claim 4 wherein the inner container is comprised of materials selected from the group consisting of polyethylenes, polypropylenes, homopolymers, and copolymers thereof.

6. A method according claim 4 wherein the outer envelope has an outer layer comprised of a metal oxide together with a polymer and an inner layer comprised of polyethylene-vinyl alcohol and polypropylene.

7. A method according to claim 1 wherein the oxygen scavenger is ferrous iron in an atmosphere of at least 90% relative humidity.

8. A method according to claim 7 wherein the ferrous iron is contained in a sachet.

9. A method according to claim 1 wherein the perishable fluid comprises a lipid emulsion for parenteral administration.

10. A method according to claim 1 wherein the pyrogallol entity is selected from the group consisting of pyrogallol, gallic acid, tannin, and esters of gallic acid.

11. A method according to claim 1 wherein the iron (II) is selected from the group consisting of iron (II) sulphate, iron (II) acetate, iron (II) nitrate, iron (II) chloride, and iron (II) trifluoroacetate.

12. A method according to claim 1 wherein the acid is an organic acid having the formula $HOOC-(CR_1, R_2)_n-COOH$ wherein $n=1-4$, $R1$ is hydrogen or a hydroxyl radical, and $R2$ is hydrogen or carboxyl radical.

13. A method according to claim 1 wherein the indicator comprises iron (II) sulphate or iron (II) sulphate heptahydrate, tannin, and citric acid or citric acid 1-hydrate.

14. A method according to claim 13 wherein the ratio of iron (II) sulphate or iron (II) sulphate heptahydrate to tannin is between 4:1 and 1:2 and the ratio between citric acid or citric acid 1-hydrate to tannin is between 6:1 and 1:1.

15. A method according to claim 1 wherein the indicator further comprises a carrier agent selected from the group consisting of cold swelling starch, propylenoxide ether of starch and carboxymethyl cellulose.

* * * * *